(12) United States Patent
Münker et al.

(10) Patent No.: US 7,545,905 B2
(45) Date of Patent: Jun. 9, 2009

(54) X-RAY CT EXAMINATION INSTALLATION AND CT METHOD OF EXAMINING OBJECTS

(75) Inventors: Martin Münker, Gevelsberg (DE); Oliver Rokitta, Ennepetal (DE); Faissal Laakel, Bochum (DE)

(73) Assignee: Yxlon International X-Ray GmbH, Hamburg (DE)

( * ) Notice: Subject to any disclaimer, the term of this patent is extended or adjusted under 35 U.S.C. 154(b) by 300 days.

(21) Appl. No.: 11/499,478

(22) Filed: Aug. 3, 2006

(65) Prior Publication Data
US 2009/0074131 A1    Mar. 19, 2009

(30) Foreign Application Priority Data
Aug. 3, 2005    (DE) ................ 10 2005 036 527

(51) Int. Cl.
*G01N 23/00* (2006.01)
(52) U.S. Cl. ........................... 378/20; 378/208
(58) Field of Classification Search .............. 378/4, 378/10, 15, 17, 20, 205, 208
See application file for complete search history.

(56) References Cited

U.S. PATENT DOCUMENTS

| | | | |
|---|---|---|---|
| 5,023,895 A * | 6/1991 | McCroskey et al. ............ 378/4 |
| 5,032,990 A | 7/1991 | Eberhard et al. | |
| 5,493,593 A | 2/1996 | Müller et al. | |
| 5,740,224 A | 4/1998 | Muller et al. | |
| 7,177,388 B2 * | 2/2007 | Takagi et al. .................. 378/20 |
| 2004/0120459 A1 | 6/2004 | Crowley et al. | |
| 2004/0234025 A1 * | 11/2004 | Schroeder et al. ............. 378/20 |

FOREIGN PATENT DOCUMENTS

WO    WO 92/06636    4/1992

OTHER PUBLICATIONS

European Search Report.

* cited by examiner

*Primary Examiner*—Jurie Yun
(74) *Attorney, Agent, or Firm*—Graybeal Jackson LLP

(57) ABSTRACT

An X-ray CT examination installation, having an X-ray tube including a focus, that creates a fan beam or a conical beam which X-rays the whole of a detector at a fixed distance from the focus, and an examination carriage, for supporting an object to be examined, the carriage having an axis of rotation perpendicular to the fan beam, wherein the examination carriage can be fixed inside the fan beam close to an edge axis which meets the detector at the edge, and can be moved on a measuring line that centrally runs at an angle to a central axis which meets the detector.

The invention also relates to a CT method of examining objects, in particular of various sizes, by means of an X-ray CT examination installation generally identified above.

13 Claims, 3 Drawing Sheets

X-RAY CT EXAMINATION INSTALLATION AND CT METHOD OF EXAMINING OBJECTS

CROSS-REFERENCE TO RELATED APPLICATION

This is a utility application that claims foreign priority benefits under 35 USC §119 (a) to German Patent Application No. DE 10 2005 036 527.2, filed 3 Aug. 2005, which application is incorporated herein by reference.

BACKGROUND OF THE INVENTION

The invention relates to an X-ray CT examination installation, with an X-ray tube with a focus, which creates a fan beam or a conical beam which X-rays the whole of a detector at a fixed distance from the focus, and with an examination carriage, for recording an object to be examined, which has an axis of rotation rotatable perpendicular to the fan beam. The invention also relates to a CT method of examining objects, in particular of various size, by means of an above-named X-ray CT examination installation.

There are currently two examination methods in industrial computed tomography (CT). One is a translation/rotation tomography and the other a rotation tomography. In both cases a fan beam which X-rays the whole of a one-dimensional detector is masked before a focal point, the focus, of an X-ray source. Both the X-ray source and also the detector are fixed. An object to be examined, which is rotated about an axis perpendicular to the plane of the fan, is inserted between them into the fan beam in order that the object can be reconstructed. The distance between X-ray tube and detector can be altered, likewise the position of the object which is arranged on a turntable so that the geometric enlargement can be matched to the requirements in each case. The individual horizontal layers of the object are recorded by progressively changing the height of the object or the X-ray tube and the detector. Instead of using a fan beam it is possible to use a conical beam and to project this onto a two-dimensional detector. A layer-by-layer scanning can then be dispensed with, depending on the size of the object.

In rotation tomography a complete measured data record is thus created because the whole of the object to be examined lies in the section plane in the fan beam and projections are recorded from at least 180° plus aperture angle of the fan beam. This method is fast, but the size of the beam fan determines the maximum size of the object which can be tomographed in this arrangement. This size is also called measuring circle. The relationship also applies in reverse, i.e. in order that a larger object can be tomographed, the measuring circle must be larger, i.e. a fan beam with larger aperture angle and thus also a larger detector are used. With this method even comparatively small objects require large installations with a long detector and a large distance between focus and detector. Technical limitations result from the maximum angle of radiation of the ray source which limits the aperture angle, and the size of the detector.

If the fan beam does not cover the whole object, this fan beam can be artificially widened by moving either the detector or the object sideways. This is translation/rotation tomography. However, there must be alternating linear and rotary movements, which is time-consuming and also requires for the transverse movement a linear axis which, over the whole distance covered, must ensure with a high degree of accuracy the right-angled alignment of the axis of rotation to the plane of the fan beam.

If, instead of a two-dimensional fan beam, a three-dimensional conical beam is used, the available examination volume is confined between the focus of the X-ray source and the corners of the mostly square two-dimensional surface detector or the edge contour of an inserted image-recording device. Otherwise the above statements apply by analogy.

Given a typical size and quantity distribution of objects to be examined—there are frequently many small and few large objects—it has hitherto been necessary to design an examination installation such that the large objects can be examined in all cases. Disadvantages result from this with regard to the size of the whole examination installation and with regard to the achievable measuring time.

SUMMARY OF INVENTION

The object of the invention is to functionally simplify an X-ray CT examination installation, operated by the known tomography method, compared with the conventional design. Additionally, such a device is also to be more compact. For developments of the invention objects of different sizes are to be able to be examined more quickly. Small objects are to be able to be examined quickly and large objects only a little more slowly.

The object is achieved by an X-ray CT examination installation with the features of claim 1. Because the examination carriage inside the fan beam can be fixed close to an edge axis which meets the detector at the edge, a half-fan procedure can be carried out. This represents a limit case. Due to the symmetry of the absorption in the object the information for the other half can be calculated from the measured data for one detector half. In this case the transverse movement is not required, although the whole of the object does not lie in the beam fans. Thus smaller detectors and as a result also smaller X-ray CT examination installations can be used to examine objects of predetermined size. This leads to a cost saving vis-à-vis the X-ray CT examination installations. Because the examination carriage can be moved on a measuring line which runs at an angle to a central axis which meets the detector centrally a fixed axis for the small objects wholly covered by the fan beam is determined on which they are positioned; this leads to a facilitation of the setting. The same also applies to the larger objects in the case of which the examination carriage is positioned further outwards in the direction of the edge axis and thus a simple setting can also take place. The mechanism of the examination installation is simplified by the predetermined measuring line on which the examination carriage can be moved.

An advantageous development of the invention provides that the examination carriage can also be moved along a first measuring line which runs along the central axis and can be fixed to same. The first measuring line serves as a positioning axis. The axis of rotation need be positioned as precisely as possible so that it stands perpendicular to the plane of the fan beam only at the approached point. On the other hand, in the case of a translation/rotation tomography this must be the case during the whole transverse movement of the axis of rotation.

Because the examination carriage has two degrees of freedom inside the plane of the fan beam, the object to be examined can always be moved to a position in which the examination method that suits it, either a rotation tomography or a half-fan procedure, can be carried out. Rapid rotation tomography can be carried out for small parts which are wholly pierced by the beam fan. Larger parts can be positioned such that the half-fan procedure can be carried out. This is also significantly faster than the translation/rotation tomography method carried out hitherto for such large objects. Nor need there be a high-accuracy linear axis for the transverse movement.

A further advantageous development of the invention provides that there is only one measuring line which extends from a first point at the edge axis to a second point on the central axis. Only a single very short measuring line is thereby required which can be used for objects of varying size. This further simplifies the mechanism of the examination installation and thus reduces its costs.

A further advantageous development of the invention provides that the first point and/or the second point lie as close as possible against the detector, wherein a free rotation of the examination carriage with an object to be examined secured thereon is only just still possible. This is the optimum design of such a diagonal short measuring line, as it allows on the edge axis the maximum size of objects that is possible in a predetermined focus detector system and simultaneously also the largest possible small parts which are wholly covered by the fan beam. There thus results an optimum combination for the fastest possible examination of both small first objects and large second objects, using both the rotation tomography and also the half-fan procedure.

Additionally, the object is also achieved by a CT method with the features of claim 5. Because the axis of rotation of the examination carriage for positioning within the fan beam is spatially fixed close to the edge axis, wherein during rotation about the axis of rotation the object never projects beyond the other edge axis, the advantages already named above in relation to the X-ray CT installation according to the invention are achieved, namely the possibility of being able to use smaller detectors and consequently also a smaller-sized X-ray CT examination installation for the examination of objects of predetermined size. This leads to a cost saving vis-à-vis the known X-ray CT methods. Because the axis of rotation is moved along the measuring line which runs at an angle to the central axis and is spatially fixed at a point for positioning at which during rotation about the axis of rotation the object never projects beyond the other edge axis. The favourable half-fan procedure can thereby always be applied with the named advantages. Furthermore the axis of rotation need stand as precisely perpendicular as possible to the plane of the fan beam only at the position at which it has been positioned to examine the object.

Additionally the object is also achieved by a CT method with the features of claim 6. Because the positioning of the object depends on its size, small first objects can be positioned such that they are wholly pierced by the fan beam, which leads to a very fast examination of these small first objects. Additionally, larger second objects which are not wholly pierced by the fan beam can be positioned at the edge axis and a half-fan procedure carried out. This is also a significantly faster method than translation/rotation tomography. According to the invention it must only be guaranteed that in the case of the larger second objects the axis of rotation is positioned at the edge axis such that the measuring circle never projects beyond the other edge axis.

An advantageous development of the invention provides that a first object is arranged for examination so remote from the focus on the central axis that it just fails to project beyond the fan beam throughout the examination. It is thereby possible to tomograph a small first object of maximum size using rotation tomography.

A further advantageous development of the invention provides that a second object is arranged for examination so remote from the focus on the edge axis that it just fails to project beyond the other edge axis throughout the examination. It is thereby possible that as large as possible a second object can be tomographed by means of the half-fan procedure.

A further advantageous development of the invention provides that the axis of rotation of an object for examination is moved on a measuring line which extends linearly from a first point on the central axis, which is so remote from the detector that during the rotation a first object can be moved without colliding past the detector, to a second point on the edge axis, which is so remote from the detector that a second object can be moved without colliding past the detector. Thus—as already described above—the use of an examination installation is made possible which has as simple a mechanism as possible in which the examination carriage merely needs to be moved along a measuring line according to the size of the object to be examined.

The first point is defined such that the rotation of the first object relative to the detector still takes place without colliding and the second point is defined such that the rotation of the second object relative to the detector still just takes place without colliding. Thereby—as already stated above—the measuring line is positioned such that as large as possible first objects which are pierced by the whole fan beam, and likewise as large as possible second objects which are tomographed merely by the half-fan procedure, can be examined in the whole examination installation. The examination installation thus has as large as possible a field of use.

Further advantages and details of the invention are described with the help of the embodiment examples, described below, represented in the Figures. There are shown in:

DETAILED DESCRIPTION

Figure 1:
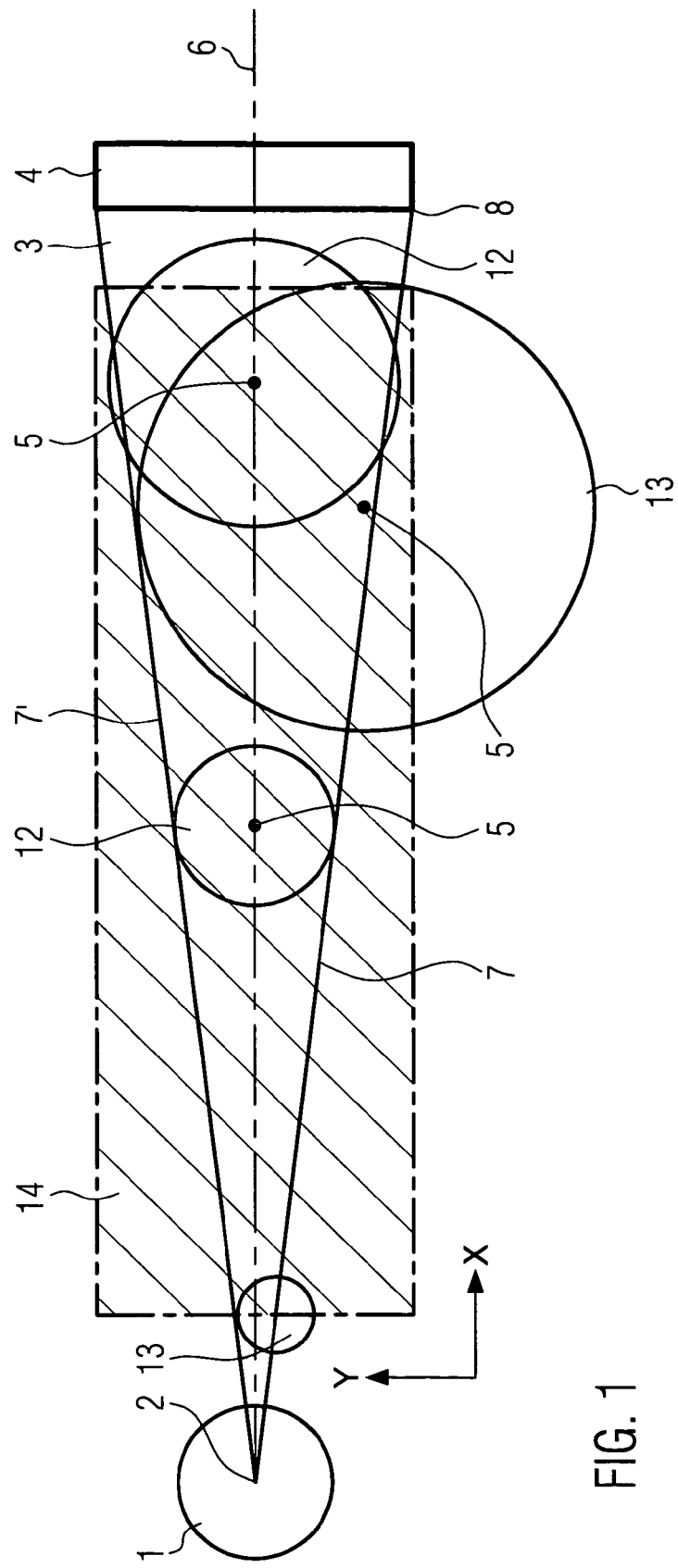
FIG. 1 a schematic top view of an X-ray CT examination installation.

A top view of an X-ray CT examination installation is schematically represented in FIG. 1. An X-ray tube 1 has a focus 2 from which an X-ray beam in the form of a fan beam 3 emanates. This fan beam 3 meets a detector 4 the whole of which is X-rayed by the fan beam 3. Such an arrangement is well known from industrial CT. The distance between detector 4 and focus 2 can be varied in order to achieve as good as possible an image geometry for an object to be examined. As only a thin slice in the plane of the fan beam 3 of the object to be examined can be tomographed by the fan beam 3 both the X-ray tube 1 and also the detector 4 can be moved vertically. The object to be examined is X-rayed layer-by-layer. Alternatively it is also possible to vary the height of the object or to combine both methods.

A carriage on which an object to be examined can be fixed is arranged between the focus 2 and the detector 4. The examination carriage rotates about an axis of rotation 5 which stands perpendicular to the plane of the fan beam 3. Data records of the object along various irradiation paths are thus generated. The object to be examined is then reconstructed from these data records. This is a nondestructive analysis of faults in the object to be examined, for example faults in a casting.

Objects differing in size have different measuring circles 12, 13. A measuring circle is determined on the one hand by the shape of the object and the axis of rotation 5 about which the object is rotated during examination. The radius of the measuring circle 12, 13 corresponds to the greatest distance of any point of the object from the axis of rotation 5. In the case of "rotation-symmetrical" rims this corresponds to the radius of the rim if the rim is attached to the examination carriage such that its centre coincides with the axis of rotation 5.

Previously it was possible to examine objects by means of a rotation tomography method whose measuring circle 12 lay wholly in the fan beam 3. This greatly limited the largest possible objects, as the largest possible objects were recordable with only a very small degree of magnification, as they had to be arranged in the immediate vicinity of the detector 4. On the other hand it was possible, with smaller objects with a smaller measuring circle 12, to also position these along a central axis 6 inside the fan beam 3 at a larger distance from the detector 4.

In order to tomograph objects with larger circles 13, it was previously necessary to use the above-described translation/rotation tomography, which was time-consuming and technically more expensive. Another possibility for such large objects was to use a half-fan procedure.

Figure 2:
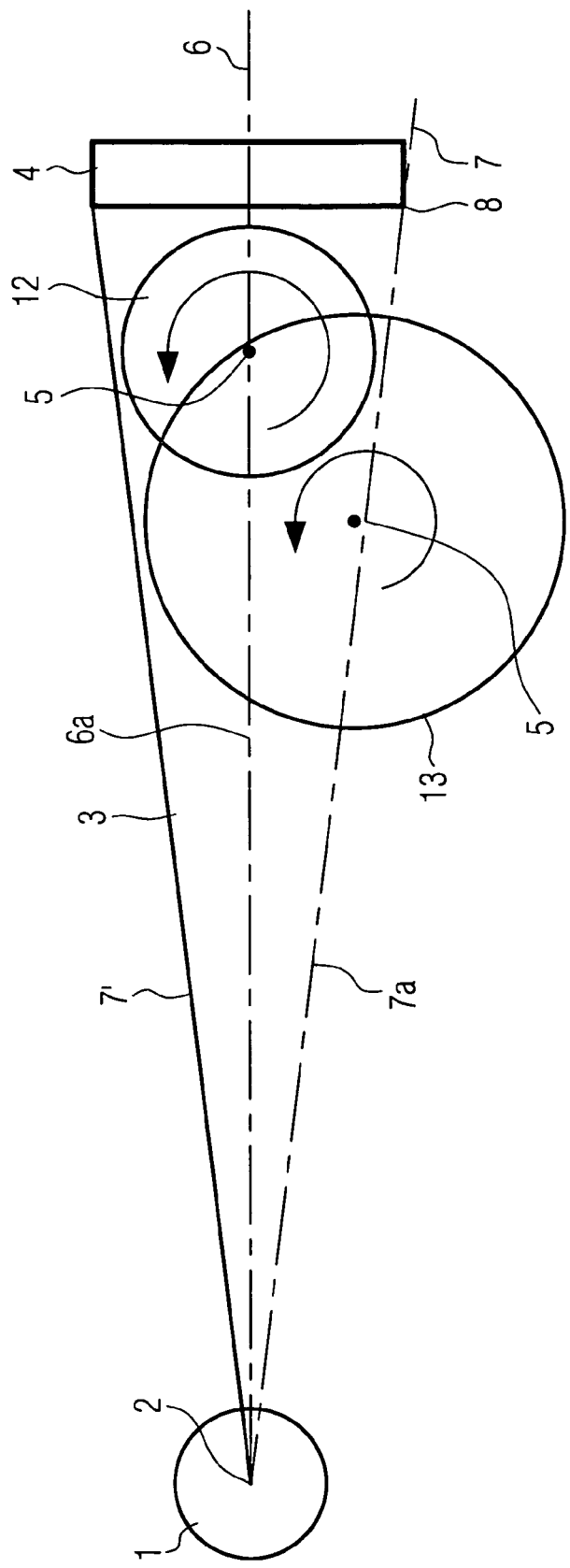
FIG. 2 a schematic top view of a first embodiment example of an X-ray CT examination installation according to the invention and FIG. 3 a schematic top view of a second embodiment example of an X-ray CT examination installation according to the invention.
Figure 3:
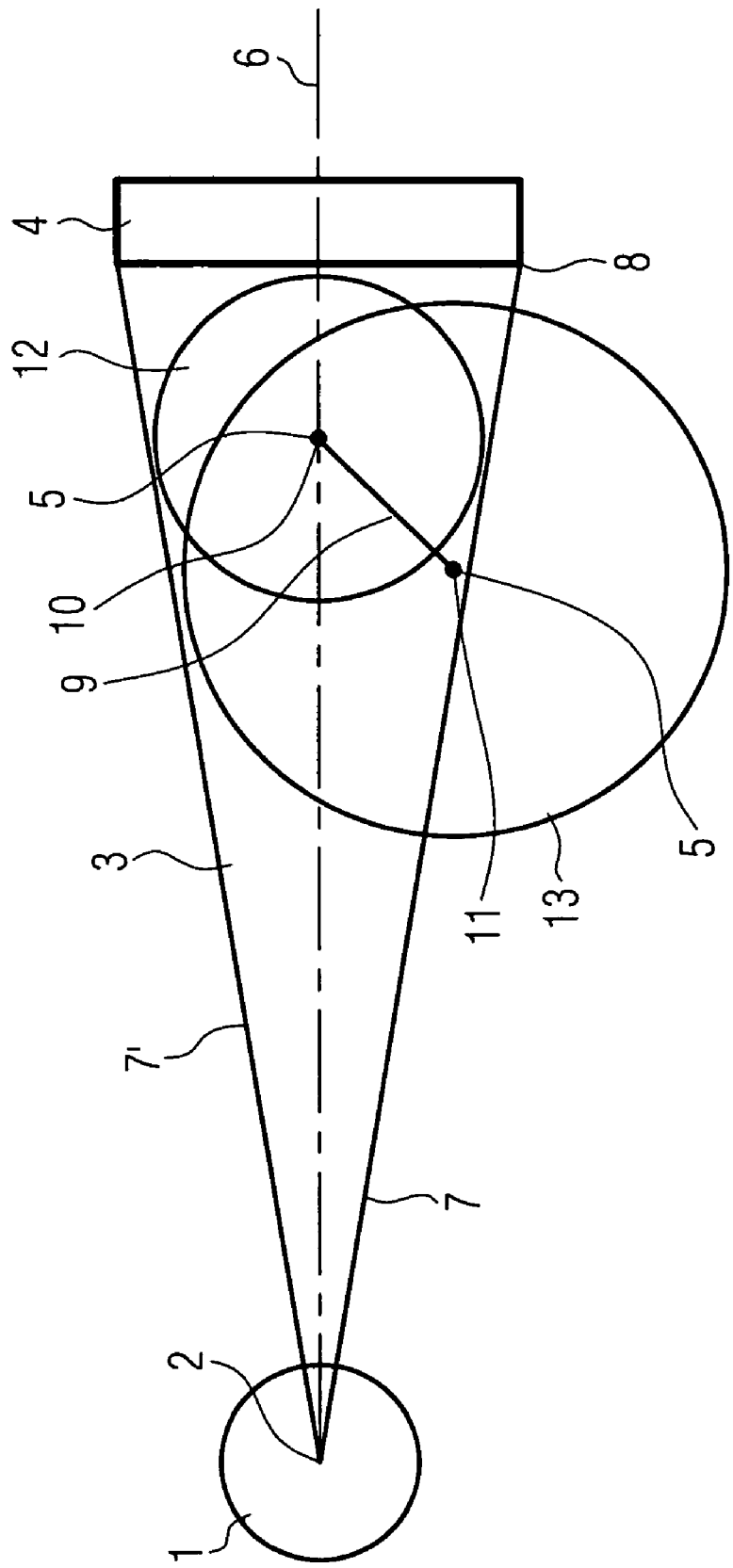

The invention according to FIGS. 2 and 3 now opens up the possibility of carrying out a rotation tomography in the same X-ray CT examination installation as a half-fan procedure. It is thereby possible to fix the suitable method individually in each case according to the size of the object and thus its measuring circle 12, 13. In order to achieve as fast a measurement as possible, a rotation tomography is regularly carried out for small objects with a first measuring circle 12 which lies wholly in the fan beam 3. However, a half-fan procedure can also be carried out with a first measuring circle 12 in the case of such larger objects if the geometric imaging conditions can then be improved in the respective application. The result is that with a half-fan procedure an object with a predetermined measuring circle 12, 13 can be arranged closer to the focus 2 and yet a reliable X-ray is still achieved.

The combination of the two different tomography methods is achieved because the examination carriage is, in principle, movable over two degrees of freedom X, Y within a positioning range 14. The theoretically possible positioning range 14 is represented hatched in FIG. 1. This merely gives the possible positions of the axis of rotation 5, but not all the points lying in the hatched positioning range 14 can also actually be approached in order to obtain a usable measurement. This is because at least half the measuring circle 13 must lie inside the fan beam 3. Thus only positions which lie inside the fan beam 3—at most just inside the two edge axes 7, 7'—are possible for the axis of rotation 5. It must additionally be guaranteed that the respective measuring circle 13 projects either beyond only edge axis 7 or the other edge axis 7', but never beyond both. Otherwise a translation/rotation tomography would have to be carried out.

With the X-ray CT examination installation according to the invention represented in FIG. 2 it is thus possible to optimally position objects with very differently-sized measurement circles 12, 13 in respect of the desired image geometry and then to tomograph them. A device on which the examination carriage moves is not essential to the invention and also well known to a person skilled in the art from the state of the art, so that it is not described in more detail here.

The first embodiment of an X-ray CT examination installation according to the invention represented in FIG. 2 is in principle structurally very similar to the installation represented in FIG. 1. For this reason, only the differences compared with the installation of FIG. 1 are described in more detail. Parts which are identical or have the same effect are given the same reference numbers.

The main difference between the installation of FIG. 1 and the first embodiment example according to the invention of FIG. 2 is that the respective examination carriage can move only along two axes. For small objects which have a first measuring circle 12 which lies wholly in the fan beam 3, the axis of rotation 5 can be positioned along a first measuring line 6a which corresponds to the central axis 6 of the detector 4. It goes without saying that the axis of rotation 5 must on the one hand be far enough from the detector 4 for the object to be able to rotate freely in or against the direction represented by an arrow. Furthermore it is clear to a person skilled in the art that the axis of rotation 5 can only approach so close to the focus 2 that the whole measuring circle 12 is still inside the fan beam 3.

For larger objects with a larger second measuring circle 13 the axis of rotation 5 can be positioned on a second measuring line 7a which runs inside the fan beam 3 and close to one of the two edge axes 7, 7'. The edge axis 7 is the axis which starts from the focus 2 and meets the edge 8 of the detector 4. Here also the axis of rotation 5 can only approach so close to the detector 4 that a free rotation of the object to be examined is possible during its rotation in or against the direction represented by an arrow. Additionally, the axis of rotation 5 can also only approach so close to the focus 2 that the measuring circle 13 does not project beyond the other edge axis 7'. Otherwise it would be necessary to carry out the expensive translation/rotation tomography.

With a design according to the second embodiment example it is even more simply possible to mechanically position the respective examination carriage, as this merely needs to be moved along an axis, either of the first measuring line 6a or of the second measuring line 7a. The guiding of the examination carriage along an axis and the possibility of fixing it to any point of this axis is not essential to the invention and is moreover well known to a person skilled in the art, so that further details of this can be dispensed with.

A second embodiment example according to the invention of an X-ray CT examination installation is represented in FIG. 3. Its basic concept is very similar to that of the previous embodiment example, so that parts which are identical or have the same effect are given the same reference numbers. Only the differences compared with the above-named embodiment example are described below.

Instead of the examination carriage being movable along two lines of measurement 6a, 7a (see FIG. 2) according to the first embodiment example, only a single short measuring line 9 is predetermined. The measuring line 9 extends from a second point 11 close to the edge axis 7 to a first point 10 of the central axis 6. The second point 11 is chosen such that the second measuring circle 13 does not overlap the detector 4, i.e. a collision-free rotation of the object during a rotation about the axis of rotation 5 which is located at the second point 11 is made possible. Naturally it also again applies—as in the previous embodiment example—that only objects with a second measuring circle 13 which does not project beyond the other edge axis 7' can be used. Thus the choice of the second point 11 determines the greatest possible extent of the object to be examined. In the represented embodiment example it would have been possible to move the second point 11a little closer to the detector 4. Thereby it would be possible to examine objects with an even larger second measuring circle 13.

The first point 10 is fixed such that a measuring circle 12 of an object to be examined does not overlap the detector 4 and simultaneously does not project beyond the edge axes 7, 7'. Through the choice of this first point 10 the size of the objects which can be examined by the especially fast rotation tomography is limited. In the represented embodiment example the first measuring circle 12 is almost as large as possible. It would be possible to go a bit further with the first point 10 in the direction of the detector 4 and thus X-ray a few larger objects by means of rotation tomography.

It would naturally be just as possible to fix both the first point 10 and also the second point 11 further away from the detector, i.e. onto the focus 2. Another image geometry is thereby obtained with a greater magnification wherein, however, the largest size of the first measuring circle 12 and of the second measuring circle 13 would be reduced. However, this is sufficient under certain circumstances, because the objects to be examined do not necessarily require a maximum size of the respective measuring circle 12, 13. Thus the alignment of the measuring line 9 can be individually chosen according to the distribution of the values of the differently-sized objects to be measured. An examination installation and a method are thus available with which an optimum examination of objects of different sizes can be achieved very easily for a small mechanical outlay.

It goes without saying that a specific object can be positioned anywhere along the measuring line 9 in order to carry out this examination. The object merely has to satisfy the condition that the associated measuring circle 13 does not project beyond the other edge axis 7'.

The resulting advantage in the represented second embodiment example is that the measuring line 9 aligned at an angle to the central beam 6 means that a smaller distance can be chosen between focus 2 and detector 4, resulting in a compact design of the X-ray CT examination installation.

It is clear to a person skilled in the art that the invention and in particular the two represented embodiment examples can also be carried out with a conical beam instead of a fan beam 3. Then, under certain circumstances, a layered X-ray of the object can even be dispensed with if the object is wholly contained in the conical beam. A square two-dimensional detector is then mostly used instead of a one-dimensional detector 4. However, this is well known from the state of the art and thus need not be described in more detail here.

It may also be pointed out that in particular a design according to the first embodiment example of FIG. 2 can also only permit a movement of the examination carriage along the edge axis 7, 7'. The examination carriage is then fixed for the examination and the object rotated about the axis of rotation 5 which is also aligned as precisely perpendicular as possible to the plane of the fan beam 3. It may also be expedient, in extreme cases, not to actually permit any movement at all of the examination carriage. The axis of rotation 5 is then to be fixed at only a single point for an examination. A very simple structure of the X-ray CT examination installation is thereby guaranteed in which the half-fan procedure can be carried out with the known advantages.

The invention claimed is:

1. X-ray CT examination installation, with an X-ray tube with a focus, which creates a fan beam or a conical beam which X-rays the whole of a detector at a fixed distance from the focus, and with an examination carriage, for supporting an object to be examined, which has an axis of rotation rotatable perpendicular to the fan beam, wherein the examination carriage has a fixing device positioned inside the fan beam close to an edge axis which meets the detector at the edge, characterized in that the examination carriage has a moving device allowing it to be moved on a measuring line which runs diagonally at an angle to a central axis which centrally meets the detector.

2. X-ray CT examination installation according to claim 1, characterized in that the examination carriage has another moving device allowing it to be moved along a first measuring line which runs along the central axis and can be fixed to same.

3. X-ray CT examination installation according to claim 1, characterized in that there is only one measuring line which extends from a first point at the edge axis to a second point on the central axis.

4. X-ray CT examination installation according to claim 3, characterized in that the first point and/or the second point lie as close as possible against the detector yet still permit a free rotation of the examination carriage with an object to be examined secured thereon.

5. CT method of examining objects by means of an X-ray CT examination installation according to claim 1, wherein, after positioning for examination, the object is rotated about the axis of rotation of the examination carriage, the axis of rotation of the examination carriage, for positioning within the fan beam, is spatially fixed close to the edge axis, wherein, during rotation about the axis of rotation, the object never projects beyond the other edge axis, characterized in that the axis of rotation is moved along the measuring line which runs diagonally at an angle to the central axis and is spatially fixed at a point for positioning at which, during rotation about the axis of rotation, the object never projects beyond the other edge axis.

6. CT method of examining objects of various sizes by means of an X-ray CT examination installation according to one of the previous claims, characterized in that the positioning of the object depends on its size and, after positioning for examination, the object is rotated about the axis of rotation of the examination carriage, wherein the axis of rotation, in the case of first objects which are so small that they are wholly covered by the fan beam or conical beam during the rotation about the axis of rotation, is positioned on the central axis;

the axis of rotation, in the case of larger second objects, is positioned by means of the examination carriage between the central axis and the edge axis such that the distance between the axis of rotation and the focus is so great that the second object never projects beyond the other edge axis during the rotation about the axis of rotation.

7. CT method according to claim 6, characterized in that a first object is arranged for examination so remote from the focus on the central axis that it just fails to project beyond the fan beam throughout the examination.

8. CT method according to claim 6 characterized in that a second object is arranged for examination so remote from the focus on the edge axis that it just fails to project beyond the other edge axis throughout the examination.

9. CT method according to claim 6, characterized in that the axis of rotation of an object for examination is moved on a measuring line which extends linearly from a first point on the central axis which is so remote from the detector that during rotation a first object can be moved without colliding past the detector to a second point on the edge axis, which is so remote from the detector that during rotation a second object can be moved without colliding past the detector.

10. CT method according to claim 7 characterized in that a second object is arranged for examination so remote from the focus on the edge axis that it just fails to project beyond the other edge axis throughout the examination.

11. CT method according to claim 7, characterized in that the axis of rotation of an object for examination is moved on a measuring line which extends linearly from a first point on the central axis which is so remote from the detector that during rotation a first object can be moved without colliding past the detector to a second point on the edge axis, which is so remote from the detector that during rotation a second object can be moved without colliding past the detector.

12. CT method according to claim 8, characterized in that the axis of rotation of an object for examination is moved on a measuring line which extends linearly from a first point on the central axis which is so remote from the detector that during rotation a first object can be moved without colliding past the detector to a second point on the edge axis, which is so remote from the detector that during rotation a second object can be moved without colliding past the detector.

13. CT method according to claim 10, characterized in that the axis of rotation of an object for examination is moved on a measuring line which extends linearly from a first point on the central axis which is so remote from the detector that during rotation a first object can be moved without colliding past the detector to a second point on the edge axis, which is so remote from the detector that during rotation a second object can be moved without colliding past the detector.

* * * * *